(12) United States Patent
Bishay et al.

(10) Patent No.: US 6,522,927 B1
(45) Date of Patent: Feb. 18, 2003

(54) ELECTRODE ASSEMBLY FOR A PERCUTANEOUS ELECTRICAL THERAPY SYSTEM

(75) Inventors: Jon M. Bishay, Woodinville, WA (US); Paul Leonard, Woodinville, WA (US)

(73) Assignee: Vertis Neuroscience, Inc., Seattle, WA (US)

(*) Notice: Subject to any disclaimer, the term of this patent is extended or adjusted under 35 U.S.C. 154(b) by 0 days.

(21) Appl. No.: 09/451,800

(22) Filed: Dec. 1, 1999

(51) Int. Cl.⁷ .................................................. A61N 1/18
(52) U.S. Cl. ........................ 607/46; 607/149; 607/145; 607/115
(58) Field of Search ............................ 607/46, 115, 145, 607/148, 149; 128/907, DIG. 26; 600/386, 372, 382, 548

(56) References Cited

U.S. PATENT DOCUMENTS

| | | | |
|---|---|---|---|
| 3,030,959 A | | 4/1962 | Grunert ........................ 606/182 |
| 3,090,151 A | | 5/1963 | Stewart et al. .................... 43/6 |
| 3,208,452 A | | 9/1965 | Stern ........................... 606/182 |
| 3,938,526 A | | 2/1976 | Anderson et al. ............ 606/189 |
| 3,943,935 A | | 3/1976 | Carmeron ..................... 606/188 |
| 3,983,881 A | | 10/1976 | Wickham ....................... 607/43 |
| 4,139,011 A | * | 2/1979 | Benoit et al. ............. 128/329 R |
| 4,207,903 A | | 6/1980 | O'Neill ........................ 607/131 |
| 4,256,116 A | | 3/1981 | Meretsky et al. .............. 607/46 |
| 4,262,672 A | | 4/1981 | Kief |

(List continued on next page.)

FOREIGN PATENT DOCUMENTS

| | | | | |
|---|---|---|---|---|
| FR | 2 500 309 | 8/1982 | ............ | A61N/1/32 |
| FR | 2500745 | 9/1982 | ........... | A61H/39/00 |
| GB | 2 163 355 A | 7/1985 | ............ | A61N/1/05 |
| GB | 2 255 719 A | 5/1991 | ............ | A61N/1/32 |

OTHER PUBLICATIONS

PCT International Search Report for International Application No. PCT/US01/31441; mailed May 7, 2002; Applicant: Vertis Neuroscience, Inc.; 8 pages.
AAMI Neurosurgery Committee; AAMI Implantable Neurostimulator Subcommittee. Implantable peripheral nerve stimulators. Assoc. for the Advancement of Medical Instrumentation (1995) NS15–1995, cover–8, 11 pages.**
Almay, B.G.L. et al., "Long–Term High Frequency Transcutaneous Electrical Nerve Stimulation (hi–TNS) in Chronic Pain. Clinical Response and Effects of CSF–Endorphins, Monoamine Metabolites, Substance P–Like Immunoreactivity (SPLI) and Pain Measures", J. Physchosom.Res. (1985) 29:247–257, 11 pages.
Baker, L. et al., "Effects of Waveform on Comfort During Neuromuscular Electrical Stimulation", Clinical Orthopedics and Related Research (Aug. 1988) 233:75–85.

(List continued on next page.)

Primary Examiner—Carl Layno
(74) Attorney, Agent, or Firm—Perkins Coie LLP (57) ABSTRACT

The invention is a percutaneous electrode assembly. In a preferred embodiment, the assembly includes a housing adapted to be mounted on a patient; an electrode disposed in the housing, the electrode having an sharp point at a distal end adapted to be inserted into a patient's tissue; an electrode actuator disposed in the housing and adapted to move the sharp point of the electrode out of the housing; and an electrode electrical connector adapted to electrically connect the electrode to a control unit to deliver electrical therapy to a patient.

The invention is also a method of inserting a percutaneous electrode into a patient. In a preferred embodiment, the method includes the following steps: placing a housing on a patient; and moving at least part of an electrode out of the housing and into the patient and connecting the electrode electrically with a control unit cable, the moving and connecting steps being performed with a single user motion.

8 Claims, 5 Drawing Sheets

U.S. PATENT DOCUMENTS

| | | | |
|---|---|---|---|
| 4,281,659 A | 8/1981 | Farrar et al. | 600/351 |
| 4,381,012 A | 4/1983 | Russek | 600/382 |
| 4,408,617 A | 10/1983 | Auguste | 600/548 |
| 4,431,000 A | 2/1984 | Butler et al. | 607/73 |
| 4,437,467 A | 3/1984 | Helfer et al. | 600/376 |
| 4,512,351 A | 4/1985 | Pohndorf | 607/117 |
| 4,541,432 A | 9/1985 | Molina-Negro et al. | 607/46 |
| 4,556,064 A | 12/1985 | Pomeranz et al. | 607/66 |
| 4,583,549 A | 4/1986 | Manoli | 600/391 |
| 4,685,466 A | 8/1987 | Rau | 600/387 |
| 4,686,996 A | 8/1987 | Ulbrich | 600/376 |
| 4,712,558 A | 12/1987 | Kidd et al. | 607/48 |
| D297,047 S | 8/1988 | Hon et al. | D24/187 |
| 4,765,310 A | 8/1988 | Deagle et al. | |
| 4,895,154 A | 1/1990 | Bartelt et al. | 607/50 |
| 4,934,371 A | 6/1990 | Malis et al. | 600/386 |
| 4,949,734 A | 8/1990 | Bernstein | 128/897 |
| 4,953,564 A | 9/1990 | Berthelsen | 607/120 |
| 5,012,811 A | 5/1991 | Malis et al. | 600/376 |
| D318,330 S | 7/1991 | Doty et al. | D24/187 |
| 5,036,850 A | 8/1991 | Owens | 607/66 |
| 5,054,486 A | 10/1991 | Yamada | 607/3 |
| 5,094,242 A | 3/1992 | Gleason et al. | |
| 5,117,826 A | 6/1992 | Bartelt et al. | 607/46 |
| 5,211,175 A | 5/1993 | Gleason et al. | |
| 5,246,014 A | 9/1993 | Williams et al. | 607/22 |
| 5,255,691 A | 10/1993 | Otten | 607/117 |
| 5,269,304 A | 12/1993 | Matthews | 607/46 |
| 5,281,218 A | 1/1994 | Imran | 606/41 |
| 5,332,401 A | 7/1994 | Davey et al. | |
| D357,069 S | 4/1995 | Plahn et al. | D24/187 |
| 5,417,719 A | 5/1995 | Hull et al. | 607/46 |
| 5,423,314 A | 6/1995 | Schmid | 600/376 |
| 5,439,440 A | 8/1995 | Hofmann | 604/20 |
| 5,449,378 A | 9/1995 | Schouenborg | |
| 5,593,429 A | 1/1997 | Ruff | 607/116 |
| 5,649,936 A | 7/1997 | Real | 606/130 |
| 5,682,233 A | 10/1997 | Brinda | 356/246 |
| 5,702,359 A | 12/1997 | Hofmann et al. | 604/20 |
| 5,810,762 A | 9/1998 | Hofmann | 604/20 |
| 5,861,015 A | 1/1999 | Benja-Athon | |
| 5,873,849 A | 2/1999 | Bernard | 604/20 |
| 5,928,144 A * | 7/1999 | Real | 600/378 |
| 5,941,845 A | 8/1999 | Tu et al. | 600/374 |
| 5,948,008 A | 9/1999 | Daikuzono | 607/89 |
| 5,968,063 A * | 10/1999 | Chu et al. | 606/185 |
| 6,009,347 A | 12/1999 | Hofmann | 604/21 |
| 6,032,064 A | 2/2000 | Devlin et al. | 600/383 |
| 6,035,236 A | 3/2000 | Jarding et al. | 607/53 |
| 6,050,992 A | 4/2000 | Nichols | 606/41 |
| 6,068,650 A | 5/2000 | Hofmann et al. | 607/2 |
| 6,117,077 A | 9/2000 | Del Mar et al. | 600/301 |
| 6,122,547 A | 9/2000 | Beja-Athon | 607/46 |
| 6,208,893 B1 | 3/2001 | Hofmann | 604/21 |
| 6,219,569 B1 | 4/2001 | Kelly et al. | 600/386 |
| D443,063 S | 5/2001 | Pisani et al. | D24/187 |
| 6,304,785 B1 | 10/2001 | McCreery et al. | 607/116 |
| 6,341,237 B1 | 1/2002 | Hurtado | 607/148 |

OTHER PUBLICATIONS

Balogun, J., "Effects of Ramp Time on Sensory, Motor and Tolerance Thresholds During Exogenous Electrical Stimulation", The Journal of Sports Medicine and Physical Fitness (Dec. 1991) 3:4, 521–526.

BD Safety Products. BD Vacutainer Safety–Lok Blood Collection Set; BD Vacutainer SafetyGlide Blood Collection Assembly and BD Vacutainer Eclipse Blood Collection Needle, 1 page.

BD Safety Flow Lancet—Product Number 366356. BD catalog 1997–2000, Capillary Access, http://catalog.bd.com/scripts/OBDsheet.exe?FNC=productlist_Alistproducts_html_366356 (Aug. 7, 2001) (3 pages).

BD Vacutainer SafetyGlide Blood Collection Assembly. Quick Reference Card (1999), 1 page.

Brull, S., Silverman, D.G., "Pulse Width, Stimulus Intensity, Electrode Placement, and Polarity During Assessment of Neuromuscular Block", Anesthesiology (Oct. 1995) 83:702–709.

Carroll, D., "Randomization is Important in Studies with Pain Outcomes: Systematic Review of Transcutaneous Electrical Nerve Stimulation in Acute Postoperative Pain", Br J Anaesth. (1996) 77:798–803**.

Cassuto, J. et al., "The Use of Modulated Energy Carried on a High Frequency Wave for the Relief of Intractable Pain", Int.J.Clin.Pharm.Res. (1993) XIII(4) 239–241**.

Cramp AF et al., "The Effect of High and Low Frequency Transcutaneous Electrical Nerve Stimulation Upon Cutaneous Blood Flow and Skin Temperature in Healthy Subjects", Clin.Physio. (2000) 20:150–7.

Eclipse+ Dual Channel Transcutaneous Electrical Nerve Stimulator User's Manual (1993), 31 pages.**

Electrotherapy for Rehabilitation, Empi Cervical Traction, http://www.empi.com/b/b2/htm, Oct. 22, 2001, 3 pages.

EPIX XL TENS Instruction Manual, Empi, Inc. (1988), 21 pages**.

Foster, N. et al., Manipulation of Transcutaneous Electrical Nerve Stimulation Variables Has No Effect on Two Models of Experimental Pain in Humans, The Clinical Journal of Pain (1996) 12:301–310**.

Galletti S.P. et al., Highlights concerning low frequency–high intensity TENS (review). Minerva Stomatol (1995) 44:421–9**.

Ghoname et al., "Does the Stimulus Frequency Affect the Analgesic Response to Electrical Stimulation?", Anesth. Analg. (1999) 88:S210, 1 page.

Gopalkrishnann, P., Sluka, K.A., "Effect of Varying Frequency, Intensity, and Pulse Duration of Transcutaneous Electrical Nerve Stimulation on Primary Hyperalgesia in Inflamed Rats", Arch.,Phys.Med.Rehabil. (Jul. 2000) 81:984–990.

Gracanin, F., Trnkoczy, A. "Optimal Stimulus Parameters for Minimum Pain in the Chronic Stimulation of Innervated Muscle", Arch.Phys.Med. Rehabil. (Jun. 1975) 56:243–249.

Hamza, M.A. et al., "Effect of the Duration of Electrical Stimulation on the Analgesic Response in Patients with Low Back Pain", Anesthesiology (Dec. 1999), V. 91, No. 6:1622–7.

Hamza MA et al., "Effect of the frequency of transcutaneous electrical nerve stimulation on the postoperative opioid analgesic requirement and recovery profile", Anesthesiology (Nov. 1999) 91:1232–8.

Han JS et al., "Effect of Low and High–Frequency TENS on Met–enkephalin–Arg–Phe and Dynorphin A Immunoreactivity in Human Lumbar CSF", Pain (1991) 47:295–8**.

Healthronics HANS LY257 User Manual, 15 pages.

Innovative Healthcare: Electrotherapy Pain & Rehabilitation Product Solutions from Rehabilicare. [Includes product description of SporTX and Ortho DX]. 1999, 3 pages, http://www.mvpdesign.com/sites/rehavilicare/all_products.html.

Instruction Manual for the Empi EPIX VT TENS Device, 1997, Dual Channel Transcutaneous Electrical Nerve Stimulator, Empi, Inc., 29 pages.**

Intelect Legend Stim Clinical Reference Manual, vol. 4 Intelect Legend Series, Chattanooga Group, Inc., 31 pages.

Jette, D., "Effect of Different Forms of Transcutaneous Electrical Nerve Stimulation on Experimental Pain", Physical Therapy (Feb. 1986) 66:2, 187–193.

Johnson, M.I., "Analgesic Effects of Different Pulse Patterns of Trancutaneous Electrical Nerve Stimulation on Cold–induced Pain in Normal Subjects", Journal of Psychosomatic Research (1991) 35:2–3; 313–321**.

Johnson, MI, "Analgesic Effects fo Different Frequencies of Transcutaneous Electrical Nerve Stimulation on Cold–Induced Pain in Normal Subjects", Pain (1989) 39:231–6**.

Johnson, MI, et al. "An In–Depth Study of Long Term Users of Transcutaneous Electrical Nerve Stimulation (TENS). Implications for Clinical Use of TENS", Pain (1991) 44:221–9**.

Katims, J.J. et al., "Transcutaneous Nerve Stimulation. Frequency and Waveform Specificity in Humans", Appl. Neurophysiol (1986) 49:86–91**.

Leem, J., "Electrophysiological evidence for the antinociceptive effect of transcutaneous electrical stimulation on mechanically evoked responsiveness of dorsal horn neurons in neuropathic rats", Neuroscience Letters (1995) 192:197–200**.

Liss S., Liss B., "Physiological and Therapeutic Effects of High Frequency Electrical Pulses", Integr.Physio.Behav. Sci (Apr.–Jun. 1996) 31:88–94.

Model AWQ–104B Multi–Purpose Electronic Acupunctoscope Instruction Manual, 10 pages.

Marchand, S., et al., "Modulation of Heat Pain Perception by High Frequency Transcutaneous Electrical Nerve Stimulation (TENS)", Clin.J.Pain (1991) 7:122–9**.

Moreno–Aranda J., "Electrical Parameters for over–the–skin muscle stimulation", J. Biomechanics (1981) 14:9, 579–585**.

Moreno–Aranda J., Seireg, A., "Investigation of over–the–skin electrical stimulation parameters for different normal muscles and subjects", J. Biomechanics (1981) 14:9; 587–593**.

O'Brien, WJ, "Effect of Transcutaneous Electrical Nerve Stimulation of Human Blood B–Endorphin Levels", Physical Therapy (Sep. 1984) 64:1367–1374.

Ordog, G., "Transcutaneous Electrical Nerve Stimulation Versus Oral Analgesic: A Randomized Double–Blind Controlled Study in Acute Traumatic Pain", American Journal of Emergency Medicine (Jan. 1987) 5:1, 6–10.

Ortho DX Product Data Sheet.

Pointer F–3 Instruction Manual, ITO Co., Ltd., 10 pages.

Rooney, J.G., et al., "Effect of Variation in the Burst and Carrier Frequency Modes of Neuromuscular Electrical Stimulation on Pain Perception of Healthy Subjects", Phsy.Ther. (Nov. 1992) 72:11, 800–808.

Sluka, K.A., "Treatment with Either High or Low Frequency TENS Reduces the Secondary Hyperalgesia Observed After Injection of Kaolin and Carrageenan into the Knee Joint", Pain (1998) 77:97–102.

SMP–plus. The Pain Relief Solution for Hard to Treat Patients, Rehabilicare (2 pages).

Somers, D.L., "High–Frequency Transcutaneous Electrical Nerve Stimulation Alters Thermal but not Mechanical Allodynia Following Chronic Constriction Injury of the Rat Sciatic Nerve", Arch.Phys.Med.Rehabil. (Nov. 1998) 79:1370–6.

SPORTX Product Data Sheet.

Starobinets, M., Volkova, L., [Analgesic Effect of High–Frequency and Acupuncture–Like Transcutaneous Electric Stimulation of Nerve Fibers in Spinal Osteochondritis]. Zh Nevropatol Psikhiatr Im S. S. Korsakova (1985) 85–350–4**.

Van Doren, CL, "Contours of Equal Perceived Amplitude and Equal Perceived Frequency for Electrocutaneous Stimuli", Percept.Phychophys. (1997) 59::613–22**.

White, P.F. et al., "Percutaneous Neuromodulation Therapy: Does the Location of Electrical Stimulation Effect the Acute Analgesic Response?", Anesth. Analg. (2000) 91:1–6.

White, P.F. et al., "The Effect of Montage on the Analgesic Response to Percutaneous Neuromodulation Therapy", Anesth. Analg. (2001) 92:483–7.

U.S. patent application Ser. No. 09/452,663, entitled "Percutaneous Electrical Therapy System with Electrode Entry Angle Control," filed on Dec. 1, 1999, Attorney Docket No. 337348004US.

U.S. patent application Ser. No. 09/452,663, entitled "Percutaneous Electrical Therapy System Providing Electrode Axial Support," filed on Dec. 1, 1999, Attorney Docket No. 337348005US.

U.S. patent application Ser. No. 09/452,508, entitled "Percutaneous Electrical Therapy System With Electrode Depth Control," filed on Dec. 1, 1999, Attorney Docket No. 337348006US.

U.S. patent application Ser. No. 09/451,795, entitled "Percutaneous Electrical Therapy System With Position Maintenance," filed on Dec. 1, 1999, Attorney Docket No. 337348007US.

U.S. patent application Ser. No. 09/451,799, entitled "Electrode Introducer for A Percutaneous Electrical Therapy System," filed on Dec. 1, 1999, Attorney Docket No. 337348008US.

U.S. patent application Ser. No. 09/452,510, entitled "Percutaneous Electrical Therapy System For Minimizing Electrode Insertion Discomfort," filed on Dec. 1, 1999, Attorney Docket No. 337348009US.

U.S. patent application Ser. No. 09/451,796, entitled "Electrode Remover for a Percutaneous Electrical Therapy System," filed on Dec. 1, 1999, Attorney Docket No. 337348011US.

U.S. patent application Ser. No. 09/451,547, entitled "Percutaneous Electrical Therapy System With Sharp Point Protection," filed on Dec. 1, 1999, Attorney Docket No. 337348012US.

Ahmed et al., "Percutaneous Electrical Nerve Stimulation (PENS): A Complementary Therapy for the Management of Pain Secondary to Bony Metastasis," Clinical Journal of Pain 14:320–3 (1998).

Ahmed et al., "Percutaneous Electrical Nerve Stimulation: An Alternative to Antiviral Drugs for Herpes Zoster," Anesth. Analg. 87:911–4 (1998).

Ballegaard et al., "Acupuncture and Transcutaneous Electric Nerve Stimulation in the Treatment of Pain Associated with Chronic Pancreatitis," Scan.J.Rehab.Med. 20:1249–54 (1985).

Balogun et al., "The effects of acupunture, electroneedling and transcutaneous electrical stimulation therapies on peripheral haemodynamic functioning," Disability and Rehab. 20:41–8 (1998).

Bushnell et al., "Electrical stimulation of peripheral and central pathways for the relifef of musculoskeletal pain," Can.J.Physiol.Pharmaocl. 69:697–703 (1991).

Cheng et al., "Electrotherapy of Chronic Musculoskeletal Pain: Comparison of Electroacupuncture and Acupuncture–Like Transcutaneous Electrical Nerve Stimulation," Clin.J.Pain 2:143–9 (1987).

Cheng et al., "Electroacupunture analgesia could be mediated by at least two pain–relieving mechanisms: endorphin and non–endorphin systems," Life Sciences 25:1957–62 (1979).

Cheng et al., "Electroacupuncture elevates blood cortisol levels in naive horses; sham treatment has no effect," Intern.J.Neuroscience 10:95–7 (1980).

Gadsby et al., "Nerve stimulation for low back pain—a review," Nursing Standard 11:32–3 (1997).

Ghoname et al., "Percutaneous electrical nerve stimulation: an alternative to TENS in the management of sciatica," Pain 83:193–9 (1999).

Ghoname et al., "Percutaneous Electrical Nerve Stimulation for Low Back Pain," JAMA 281:818–23 (1999).

Ghoname et al., "The Effect of Stimulus Frequency on the Analgesic Response to Percutaneous Electrical Nerve Stimulation in Patients with Chronic Low Back Pain," Anesth.Analg. 88:841–6 (1999).

Ghoname et al., "The effect of the duration of electrical stimulation on the analgesic response," Anesth.Analg. 88:S211 (1999).

Landau et al., "Neuromodulation Techniques for Medically Refractory Chronic Pain," Annu.Rev.Med. 44:279–87 (1993).

Lehmann et al., "Efficacy of Electroacupunture and TENS in the Rehabilitation of Chronic Low Back Pain Patients," Pain 26:277–90 (1986).

Omura, "Basic electrical parameters for safe and effective electro–therapeutics [electroacupuncture, TES TENMS (or TEMS), TENS and electro–magnetic field stimulation with or without drug field] for pain, neuromuscular skeletal problems, and circulatory disturbances," Acupunture & Electro–Therapeutics Res. 12:201–25 (1987).

Omura, "Electrical parameters for safe and effective electro–acupuncture and transcutaneous electrical stimulation: Threshold potentials for tingling, muscle contraction and pain; and how to prevent adverse effects of electro–therapy," Acupuncture & Electro–Therapeutics Res. 10:335–7 (1985).

Romita et al., "Parametric Studies on Electroacupuncture–Like Stimulation in a Rat Model: Effects fo Intensity, Frequency, and Duration of Stimulation on Evoked Antinociception," Brain Res.Bull. 42:289–96 (1997).

Ulett et al., "Electroacupuncture: Mechanisms and Clinical Application," Biol.Psych. 44:129–38 (1998).

Radionics RFG–3C product brochure (1997).

Rehabilicare Ortho Dx product brochure.

Rehabilicare SporTX product brochure.

Ahmed et al., "Percutaneous Electrical Nerve Stimulation (PENS): A Complementary Therapy for the Management of Pain Secondary to Bony Metastasis," Clinical Journal of Pain 14:320–3 (1998).

Ahmed et "Percutaneous Electrical Nerve Stimulation: An Alternative to Antiviral Drugs for Herpes Zoster," Anesth. Analg. 87:911–4 (1998).

Ballegaard et al., "Acupuncture and Transcutaneous Electric Nerve Stimulation in the Treatment of Pain Associated with Chronic Pancreatitis," Scan.J.Rehab.Med. 20:1249–54 (1985).

Balogun et al., "The effects of acupuncture, electroneedling and transcutaneous electrical stimulation therapies on peripheral haemodynamic functioning," Disability and Rehab. 20:41–8 (1998).

Bushnell et al., "Electrical stimulation of peripheral and central pathways for the relief of musculoskeletal pain," Can.J.Physiol.Pharmacol. 69:697–703 (1991).

Cheng et al., "Electrotherapy of Chronic Musculoskeletal Pain: Comparison of Electroacupuncture and Acupuncture–Like Transcutaneous Electrical Nerve Stimulation," Clin. J.Pain 2:143–9 (1987).

Cheng et al., "Electroacupuncture analgesia could be mediated by at least two pain–relieving mechanisms: endorphin and non–endorphin systems," Life Sciences 25:1957–62 (1979).

Cheng et al., "Electroacupuncture elevates blood cortisol levels in naive horses; sham treatment has no effect," Intern.J.Neuroscience 10:95–7 (1980).

Gadsby et al., "Nerve stimulation for low backpain—a review," Nursing Standard 11:32–3 (1997).

Ghoname et al., "Percutaneous electrical nerve stimulation: an alternative to TENS in the management of sciatica," Pain 83:193–9 (1999).

Ghoname et al., "Percutaneous Electrical Nerve Stimulation for Low Back Pain," JAMA 281:818–23 (1999).

Ghoname et al., "The Effect of Stimulus Frequency on the Analgesic Response to Percutaneous Electrical Nerve Stimulation in Patients with Chronic Low Back Pain," Anesth. Analg. 88:841–6 (1999).

Ghoname et al., "The effect of the duration of electrical stimulation on the analgesic response," Anesth.Analg. 88:S211 (1999).

Landau et al., "Neuromodulation Techniques for Medically Refractory Chronic Pain," Annu.Rev.Med. 44:279–87 (1993).

Lehmann et al., "Efficacy of Electroacupuncture and TENS in the Rehabilitation of Chronic Low Back Pain Patients," Pain 26:277–90 (1986).

Omura, "Basic electrical parameters for safe and effective electro–therapeutics [electroacupuncture, TES, TENMS (or TEMS), TENS and electro–magnetic field stimulation with or without drug field] for pain, neuromuscular skeletal problems, and circulatory disturbances," Acupuncture & Electro–Therapeutics Res. 12:201–25 (1987).

Omura, "Electrical parameters for safe and effective electro–acupuncture and transcutaneous electrical stimulation: Threshold potentials for tingling, muscle contraction and pain; and how to prevent adverse effects of electro–therapy," Acupuncture & Electro–Therapeutics Res. 10:335–7 (1985).

Romita et al., "Parametric Studies on Electroacupuncture–Like Stimulation in a Rat Model: Effects of Intensity, Frequency, and Duration of Stimulation on Evoked Antinociception," Brain Res.Bull. 42:289–96 (1997).

Ulett et al., "Electroacupuncture: Mechanisms and Clinical Application," Biol.Psych. 44:129–38 (1998).

Radionics RFG–3C product brochure (1997).

Rehabilicare Ortho Dx product brochure.

Rehabilicare SporTX product brochure.

\* cited by examiner

ELECTRODE ASSEMBLY FOR A PERCUTANEOUS ELECTRICAL THERAPY SYSTEM

BACKGROUND OF THE INVENTION

This invention relates generally to percutaneous electrical therapy systems for medical use. In particular, the invention relates to an electrode assembly for inserting, using and removing percutaneous electrodes.

Electrical therapy has long been used in medicine to treat pain and other conditions. For example, transcutaneous electrical nerve stimulation (TENS) systems deliver electrical energy through electrode patches placed on the surface of a patient's skin to treat pain in tissue beneath and around the location of the patches. The efficacy of TENS systems in alleviating pain is questionable at best, however.

More recently, a technique in which electrodes are placed through the patient's skin into the target tissue has been proposed. Percutaneous Neuromodulation Therapy ("PNT") (also sometimes called Percutaneous Electrical Nerve Stimulation or "PENS") using percutaneously placed electrodes achieves significantly better pain relief results than TENS treatments using skin surface electrodes. This therapy is described in Ghoname et al., "Percutaneous Electrical Nerve Stimulation for Low Back Pain," JAMA 281:818–23 (1999); Ghoname et al., "The Effect of Stimulus Frequency on the Analgesic Response to Percutaneous Electrical Nerve Stimulation in Patients with Chronic Low Back Pain," Anesth. Analg. 88:841–6 (1999); Ahmed et al., "Percutaneous Electrical Nerve Stimulation (PENS): A Complementary Therapy for the Management of Pain Secondary to Bony Metastasis," Clinical Journal of Pain 14:320–3 (1998); and Ahmed et al., "Percutaneous Electrical Nerve Stimulation: An Alternative to Antiviral Drugs for Herpes Zoster," Anesth. Analg. 87:911–4 (1998). The contents of these references are incorporated herein by reference.

Thus far, PNT practitioners have used percutaneously placed acupuncture needles attached to waveform generators via cables and alligator clips to deliver the therapy to the patient. This arrangement and design of electrodes and generator is far from optimal. For example, insertion and removal of percutaneous electrodes has thus far been cumbersome and inaccurate. In addition, the prior art has not adequately addressed the issue of sharps protection for the patients' caregivers and other bystanders. It is therefore an object of this invention to reduce the exposure of electrical therapy patients' caregivers to accidental exposure to blood-borne pathogens, microbes, toxins, etc., via an injury caused by unintended contact with a sharp electrode.

It is a further object of this invention to provide a percutaneous electrical therapy system having electrodes and electrode assemblies that are safe, efficacious, inexpensive and easy to use.

Other objects of the invention will be apparent from the description of the preferred embodiments.

SUMMARY OF THE INVENTION

The invention is a percutaneous electrode assembly. In a preferred embodiment, the assembly includes a housing adapted to be mounted on a patient; an electrode disposed in the housing, the electrode having an sharp point at a distal end adapted to be inserted into a patient's tissue; an electrode actuator disposed in the housing and adapted to move the sharp point of the electrode out of the housing; and an electrode electrical connector adapted to electrically connect the electrode to a control unit to deliver electrical therapy to a patient.

In one embodiment, the assembly also includes a limit stop limiting movement of the electrode out of the housing.

The assembly may also include an actuator tool adapted to engage the actuator to move the sharp point of the electrode out of the housing. The actuator tool may have a conductor adapted to electrically communicate with the electrode electrical connector.

The invention is also a method of inserting a percutaneous electrode into a patient. In a preferred embodiment, the method includes the following steps: placing a housing on a patient; and moving at least part of an electrode out of the housing and into the patient and connecting the electrode electrically with a control unit cable, the moving and connecting steps being performed with a single user motion.

In some embodiments, the placing step includes the step of attaching the housing to the patient, such as with adhesive.

In some embodiments, the moving and connecting steps include engaging a tool to move at least a portion of the electrode out of the housing and to connect the electrode electrically with the control unit cable. If the method also includes the step of treating the patient with electrical therapy by delivering electricity to the electrode, the tool may remain engaged during treatment.

In some embodiments, the method may include the step of moving the electrode back into the housing and disconnecting the electrode electrically from the control unit cable, the steps of moving the electrode back and disconnecting the electrode being performed with a single user motion.

The invention is described in more detail below with reference to the drawings.

DETAILED DESCRIPTION OF THE PREFERRED EMBODIMENTS

Percutaneous electrical therapy systems, such as PNT systems, deliver electric current to a region of a patient's tissue through electrodes that pierce the skin covering the tissue. The electric current is generated by a control unit external to the patient and typically has particular waveform characteristics such as frequency, amplitude and pulse width. Depending on the treatment or therapy being delivered, there may be one electrode containing both a cathode and an anode or a plurality of electrodes with at least one serving as a cathode and at least one serving as an anode.

The electrode has a sharp point to facilitate insertion through the patient's skin and to enhance local current density during treatment. The depth and location of the electrode's point is critical to the therapy. This invention therefore provides a percutaneous electrode introducer that is accurate and easy to use.

In addition, once inserted into the skin, the sharp point may become exposed to pathogens, microbes, toxins, etc. in the patient's tissue and/or blood. After removal of the electrode from the patient's tissue, a caregiver or other bystander may be stuck accidentally with the sharp point of the electrode, thereby exposing the caregiver to any pathogens that may be on the used electrode. This invention therefore provides an electrode assembly for a percutaneous electrical therapy system that provides sharp point protection and is easy to use.

FIGS. 1–9 show the preferred embodiment of this invention. An electrode assembly 30 includes a base 32, an electrode 34, and a plunger or actuator 36. Base 32 has a flange or flared end 44 that is adapted to make contact with a patient's skin. Base 32 may be formed from any suitable polymer or metal, such as a high density polyethylene (HDPE). Base 32 is preferably opaque so that the electrode cannot be seen by a needle-shy patient.

Figure 1:
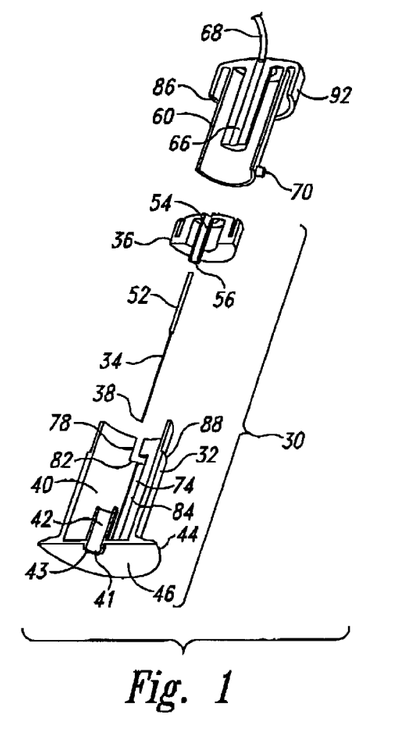
FIG. 1 is an exploded sectional view of an electrode and sharp point protection assembly according to yet another embodiment of this invention.
Figure 2:
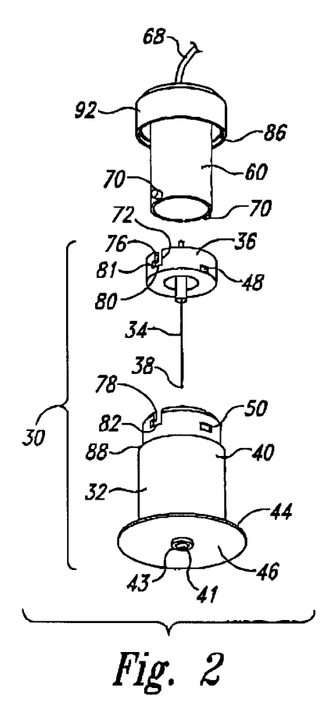
FIG. 2 is a partially exploded elevational view of the embodiment of FIG. 1.

Actuator 36 fits within a housing portion 40 of base 32 in a slidable arrangement. A locking assembly is operable to prevent relative movement between actuator 36 and housing 40 of base 32. In this embodiment, the locking assembly of actuator 36 has integrally-formed resilient detents 48 on its exterior cylindrical surface. In the undeployed state of electrode assembly 30, detents 48 mate with a corresponding openings 50 in base 32 to hold actuator 36 and base 32 in place with respect to each other to prevent electrode 34 from moving outside of the protective housing 40 of base 32 and thereby providing sharp point protection, as explained further below. Mechanisms other than the detent and opening arrangement shown here may be used to hold the actuator and base in place may be used without departing from the invention.

In this embodiment, electrode 34 is preferably a 3 cm. long 32 gauge stainless steel needle. Other sizes and materials may be used for electrode 34, of course, without departing from the scope of the invention. Actuator 36 is preferably formed from HDPE as well, although other suitable materials may be used.

Figure 4:
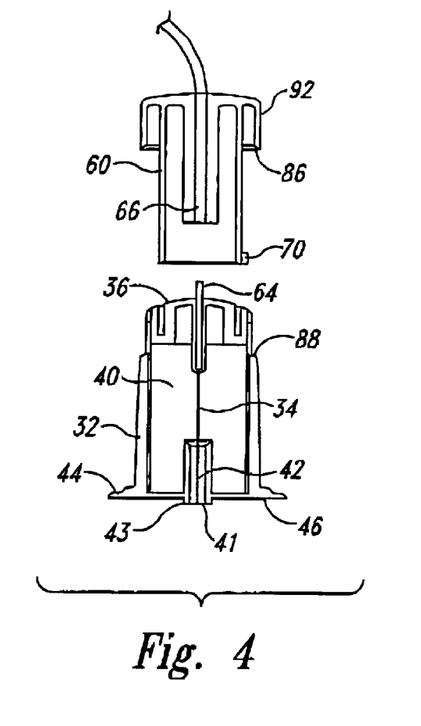
FIG. 4 is a sectional view of the embodiment of FIG. 1 showing the electrode and sharp point protection assemblies and an actuator tool.

Electrode 34 has a larger-diameter handle 52 at its proximal end. Handle 52 fits within a channel 54 formed within actuator 36. Channel 54 has a narrow opening 56 at its distal end whose diameter is slightly larger than the diameter of electrode 34 but narrower than the diameter of handle 52 to hold electrode 34 in place within actuator 36 after initial manufacture and assembly. As shown in FIG. 4, in an undeployed state the sharp point 38 of electrode 34 is disposed within housing portion 40 of base 32, specifically, within a narrow channel 42 of the housing 40.

To deploy one or more electrode assemblies on a patient in order to provide electrical stimulation therapy (such as PNT), the distal surface 46 of flange portion 44 of base 32 is mounted on the desired site on the patient's skin, preferably with a compressible adhesive pad (not shown) surrounding a ring 43 extending downward from surface 46 around an aperture 41 formed at the distal end of channel 42, although other means of attaching base 32 to the patient may be used as appropriate.

Figure 3:
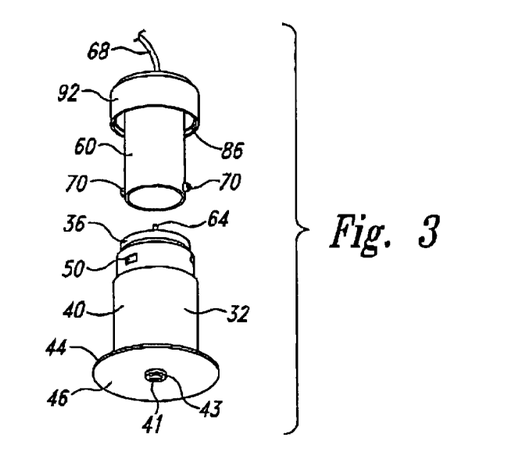
FIG. 3 is an elevational view of the embodiment of FIG. 1 showing the electrode and sharp point protection assemblies and an actuator tool.

An electrical connector and actuator tool 60 is used to insert the electrode and connect the electrode electrically with a control unit 62. Actuator tool 60 and electrode assembly 30 also interact to provide the sharp point protection assembly of this embodiment. When the distal end of actuator tool 60 is placed against the proximal ends of base 32 and actuator 36, the exposed proximal end 64 of electrode handle 52 makes electrical contact with a contact surface 66 within actuator tool 60. Contact surface 66, in turn, is electrically connected to the control unit 62 via a cable or other conductor 68.

Actuator tool 60 has two oppositely disposed pegs 70 extending outward from the distal portion of its cylindrically surface. Pegs 70 mate with two corresponding slots 72 in actuator 36 and with two corresponding grooves 74 in base 32. (The second slot 72 and second groove 74 are each opposite the slot 72 and groove 74, respectively, shown in FIGS. 4 and 5.) When connecting actuator tool 60 to electrode assembly 30, pegs 70 move along longitudinal portions 76 of slots 72 and along longitudinal portions 78 of grooves 74. Concurrently, exposed distal end 64 of electrode handle 52 begins to make sliding contact with contact surface 66 of actuator tool 60 to create the electrical connection between actuator tool 60 and electrode 32.

Figure 5:
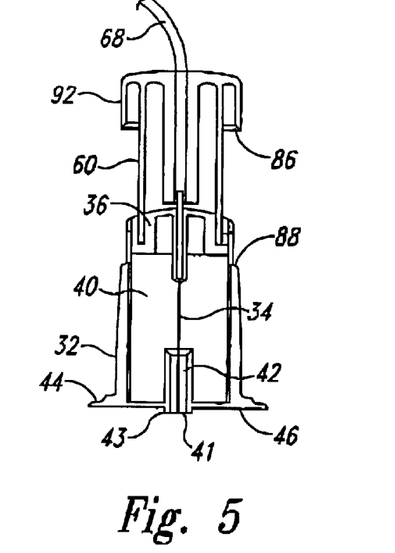
FIG. 5 is a sectional view of the embodiment of FIG. 1 showing the actuator tool in engagement with the electrode and sharp point protection assemblies prior to insertion of the electrode into a patient's tissue.

Clockwise rotation (looking down on the assembly) of actuator tool 60 after pegs 70 reach the end of longitudinal portions 76 and 78 moves pegs 70 into short circumferential portions 80 and 82, respectively, of slots 72 and grooves 74. The length of circumferential portions 80 of slots 72 is less than the length of circumferential portions 82 of grooves 74. Continued movement of pegs 70 along circumferential portions 82 will therefore move pegs 70 against the ends 81 of circumferential slots 80. Further clockwise rotation of actuator tool 60 will cause actuator 36 to rotate clockwise as well, thereby moving detents 48 out of openings 50 and allowing the electrode 34 and actuator 36 to move with respect to base 32.

Second longitudinal portions 84 of grooves 74 are formed in base 32 at the end of circumferential portions 82. Movement of pegs 70 distally along longitudinal portions 84 pushes pegs 70 against the distal edges of circumferential slot portions 80, thereby moving actuator 36 and electrode 34 distally toward the patient's skin 22.

Figure 6:
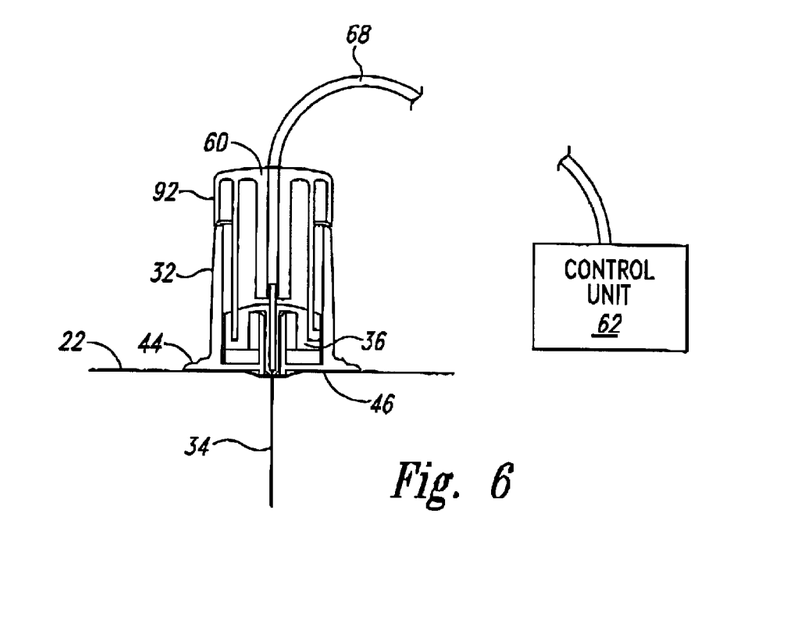
FIG. 6 is a sectional view of the embodiment of FIG. 1 with the electrode in its deployed and inserted state.

As it moves, electrode 34 passes through channel 42, and the sharp point of electrode 34 moves out through aperture 41. Channel 42 and actuator 36 provide axial support to electrode 34 during this forward movement and also, along with the support provided by flange 44, provide entry angle guidance to the electrode. In addition, downward pressure on the patient's skin during electrode deployment compresses the compressible adhesive pad and presses ring 43 against the patient's skin 22, which helps ease electrode entry through the skin and also lessens the insertion pain experienced by the patient.

Distal movement of the electrode and its actuator within base 32 continues until the distal surface 86 of a cylindrical cap portion 92 of actuator tool 60 meets an annular surface 88 of housing 40. At this point, sharp point 38 of electrode 34 has extended a predetermined depth into the tissue underlying the patient's skin. In the preferred embodiment, this predetermined depth is approximately 3 cm., although other electrode depths may be desired depending on the treatment to be performed.

The interaction of the actuator tool with the actuator and electrode enables the electrode to be inserted into the patient and connected electrically with the control unit in a single motion. From a time and motion standpoint, this design provides increased efficiency through the elimination of a motion. This efficiency can save the caregiver a great deal of time when multiplied by, e.g., ten electrodes per patient and five patients per hour.

An optional feature of the invention is a deployed electrode holding mechanism. In this embodiment, an interference fit between the inner surface of channel 42 and the outer surface 55 of channel 52 performs this function.

Electrical stimulation treatment may begin once the electrodes have been deployed and inserted. Control unit 62 supplies stimulation current to the electrodes, e.g., in the manner described in the Ghoname et al. articles. The electrical waveform provided by the control unit depends on the application. For example, in an embodiment of a system providing percutaneous neuromodulation therapy, control unit 62 would preferably provide a current-regulated and current-balanced waveform with an amplitude of up to approximately 20 mA, frequency between approximately 4 Hz and 50 Hz, and pulse width of between approximately 50 $\mu$sec and 1 msec.

The interaction of actuator tool 60 and base 32 provides stability to electrode 34 and its electrical connection to the control unit during treatment by holding the electrode in place, by providing strain relief for tugging forces on cable 68, and by providing a robust mechanical connection. It should be noted that the sharp point of the electrode is not exposed to the operator or to any other bystander at any point during deployment and use of the electrode assembly.

After treatment has been completed, the electrode may be removed from the patient. To do so, actuator tool 60 is moved proximally away from the patient. As pegs 70 move proximally along longitudinal portions 84 of grooves 74, pegs 70 push against proximal edges of the actuator's circumferential slot portions 80, thereby moving actuator 36 and electrode 34 proximally as well. When pegs reach the proximal end of longitudinal groove portions 84, the sharp end 38 of electrode 34 is out of the patient and safely inside housing 40 of base 32. Counterclockwise movement of actuator tool 60 moves pegs along circumferential portions 80 and 82 of slot 72 and groove 74, respectively. Since, as discussed above, circumferential portion 80 is shorter than circumferential portion 82, this counterclockwise movement will turn actuator 36 counterclockwise.

At the limit of the counterclockwise movement, detents 48 move back into openings 50 to prevent further movement of the electrode and actuator with respect to base 32. Further distal movement of actuator tool 60 moves pegs 70 distally along longitudinal portions 76 and 78 of slot 72 and groove 74, respectively, to disconnect actuator tool 60 from electrode assembly 30. Base 32 can then be removed from the patient.

Once again, the interaction of the actuator tool with the actuator and electrode enables the electrode to be removed from the patient and disconnected electrically from the control unit in a single motion. From a time and motion standpoint, this design provides increased efficiency through the elimination of a motion, particularly when multiplied by many electrodes and many patients.

Also, at no time during the electrode deployment, use or removal processes was the sharp point of the electrode exposed to the operator or bystanders.

Figure 7:
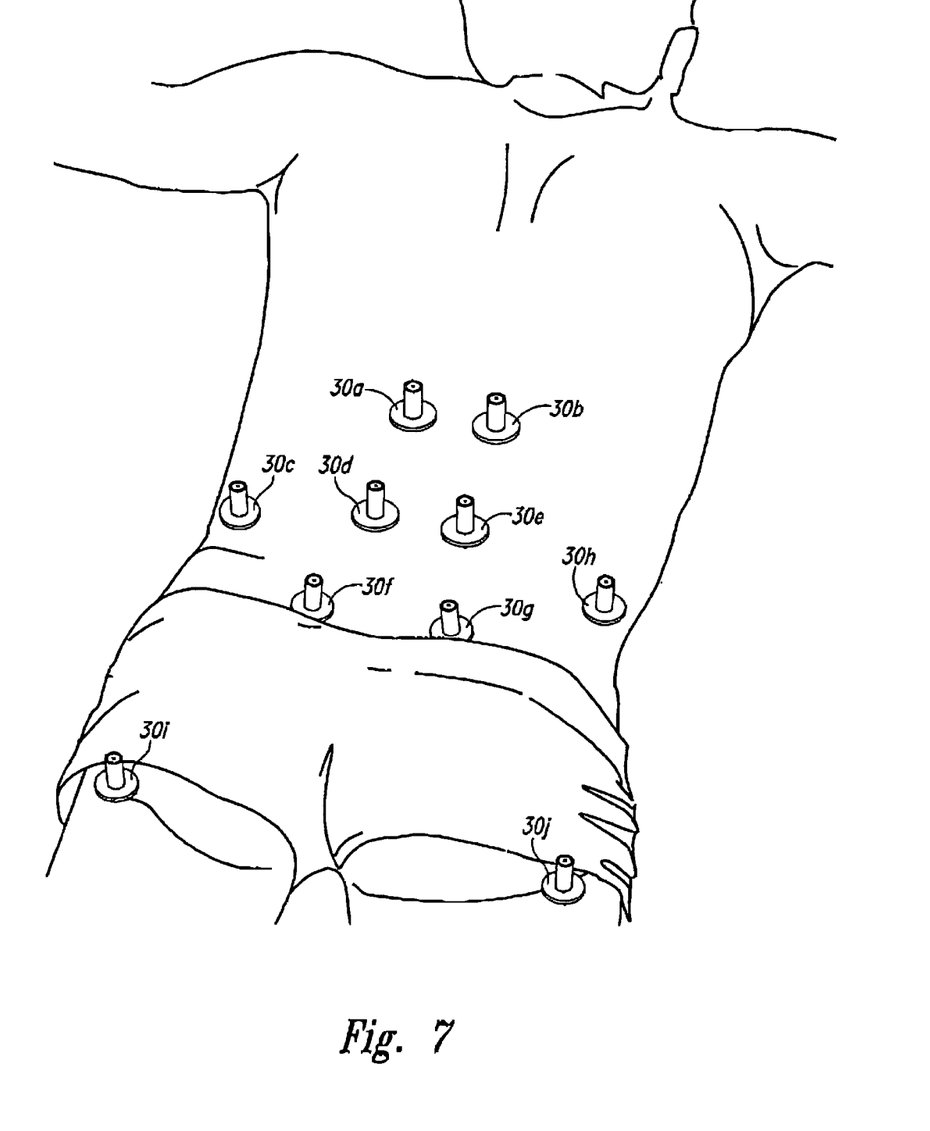
FIG. 7 shows a montage for using the embodiment of FIG. 1 to treat low back pain with the electrodes in a partially deployed but uninserted state.
Figure 8:
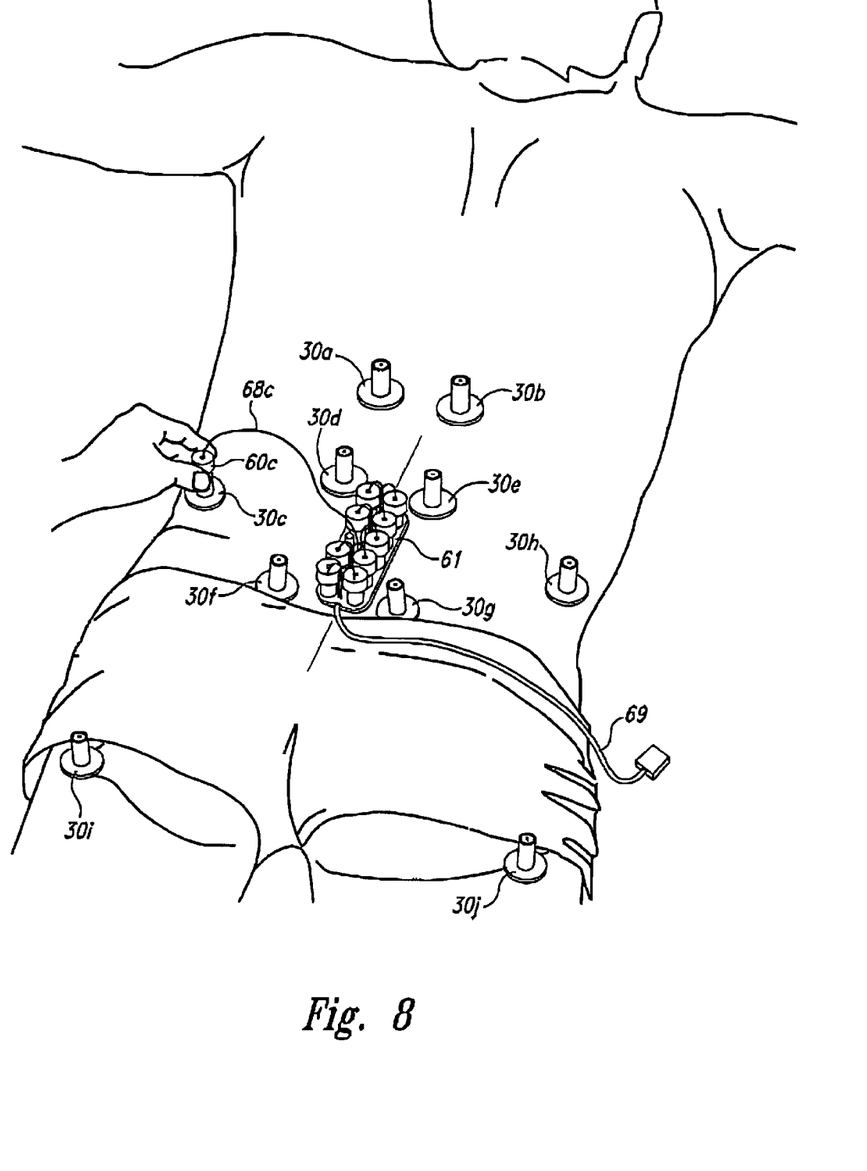
FIG. 8 shows the electrode montage of FIG. 7 at the beginning of the electrode insertion step.

FIGS. 10–12 show the use of the electrode and sharp point protection assemblies of FIGS. 4–9 to treat low back pain using PNT. As shown in FIG. 7, ten electrode assemblies 30a–j are arranged in a montage on the patient's back and attached with adhesive. Next, ten actuator tools 60a–j are attached to the ten electrode assemblies 30a–j. In this example, prior to deployment the actuator tools are mounted on an actuator tool tray 61 that provides electrical communication to a control unit 62 via cable 69. The actuator tools electrically connect with tool tray 61, and thereby to cable 69 and control unit 62, via individual cables 68a–j. It should be understood that the tool tray 61 and its electrical connection scheme play no part in the invention claimed in the presons application. FIG. 8 shows the beginning of the electrode insertion process.

Figure 9:
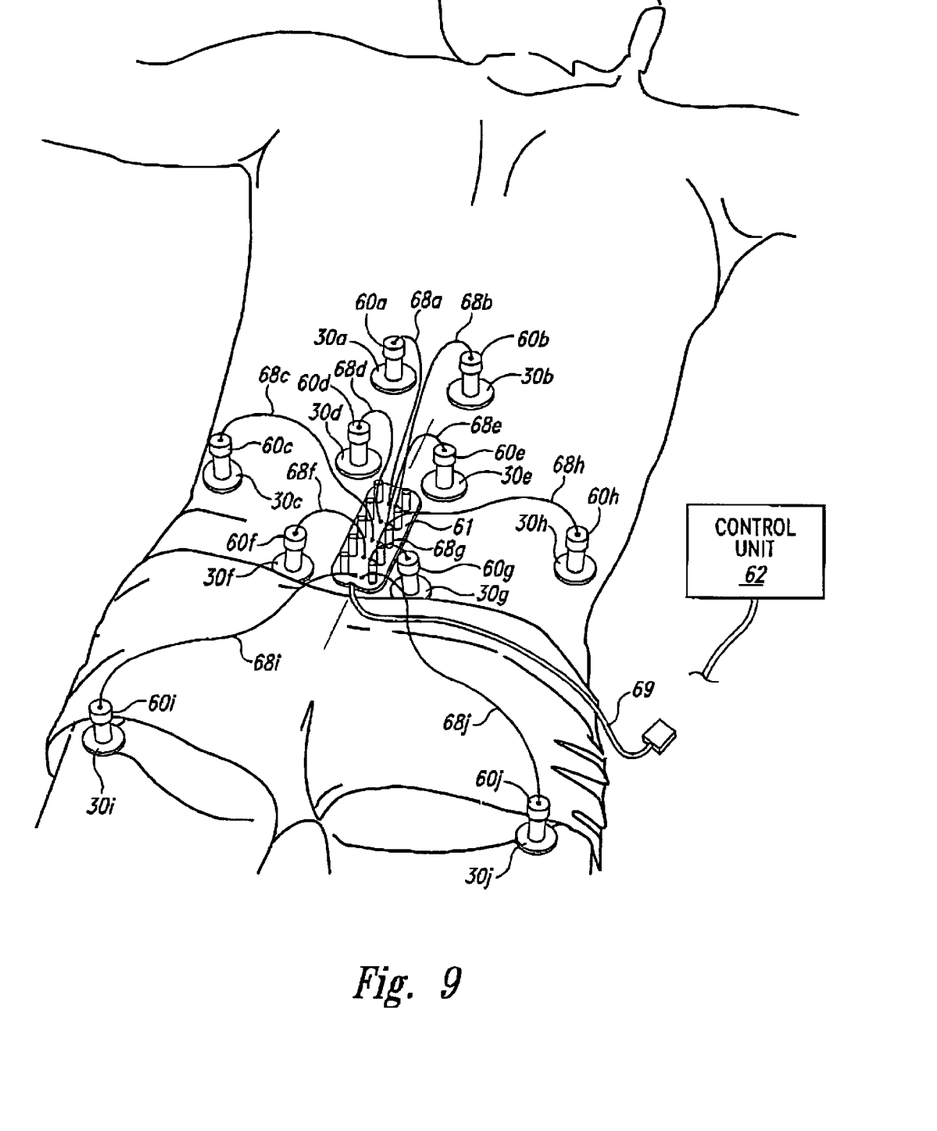
FIG. 9 shows the electrode montage of FIG. 7 with the electrodes deployed, inserted and attached to a control unit to provide electrical therapy to the patient.

Once each electrode assembly has been actuated by its respective actuator tool to insert an electrode into the patient's tissue (as shown in FIG. 9), control unit 62 provides electrical signals to treat the patient. Preferably, half the electrodes (e.g., assemblies 30b, 30d, 30g, 30h and 30i) are treated as anodes, and the other half as cathodes. In the preferred embodiment, control unit 62 would provide a current-regulated and current-balanced waveform with an amplitude of up to approximately 20 mA, frequency between approximately 4 Hz and 50 Hz, and pulse width of between approximately 50 $\mu$sec and 1 msec. to treat the patient's low back pain using PNT.

Modifications of the above embodiments of the invention will be apparent to those skilled in the art. For example, while the invention was described in the context of percutaneous electrical therapy in which electrodes are used to deliver electricity to a patient, the features of the invention may be used with electrodes designed for medical monitoring and/or diagnosis. In addition, the features of this invention may be used with acupuncture needles or other needles not used for conducting electricity to or from a patient.

What is claimed is:

1. A percutaneous electrode assembly comprising:
   a housing configured to be mounted on a patient,
   an electrode disposed in the housing, the electrode comprising a sharp point at a distal end configured to be inserted into a patients tissue;
   an electrode actuator disposed in the housing and configured to move the sharp point of the electrode out of the housing;
   an electrode electrical connector configured to electrically connect the electrode to a control unit to deliver electrical therapy to a patient; and
   a limit stop limiting movement of the electrode out of the housing.

2. The assembly of claim 1 further comprising an actuator tool configured to engage the actuator to move the sharp point of the electrode out of the housing.

3. A percutaneous electrode assembly comprising:
   a housing configured to be mounted on a patient;
   an electrode disposed in the housing, the electrode comprising an sharp point at a distal end configured to be inserted into a patient's tissue;
   an electrode actuator disposed in the housing and configured to move the sharp point of the electrode out of the housing;
   an electrode electrical connector configured to electrically connect the electrode to a control unit to deliver electrical therapy to a patient; and
   an actuator tool configured to engage the actuator to move the sharp point of the electrode out of the housing;

wherein the actuator tool comprises a conductor adapted to electrically communicate with the electrode electrical connector.

4. A method of inserting a percutaneous electrode into a patient, the method comprising:

placing a housing on a patient; and moving at least part of an electrode out of the housing and into the patient and connecting the electrode electrically with a control unit cable, the moving and connecting steps being performed with a single user motion.

5. The method of claim 4 wherein the placing step comprises attaching the housing to the patient.

6. The method of claim 4 wherein the moving and connecting steps comprise engaging a tool to move at least a portion of the electrode out of the housing and to connect the electrode electrically with the control unit cable.

7. The method of claim 6 further comprising treating the patient with electrical therapy by delivering electricity to the electrode, the tool remaining engaged during treatment.

8. The method of claim 4 further comprising:

moving the electrode back into the housing and disconnecting the electrode electrically from the control unit cable, the steps of moving the electrode back and disconnecting the electrode being performed with a single user motion.

* * * * *

UNITED STATES PATENT AND TRADEMARK OFFICE
CERTIFICATE OF CORRECTION

PATENT NO.     : 6,522,927 B1
DATED          : February 18, 2003
INVENTOR(S)    : Bishay et al.

It is certified that error appears in the above-identified patent and that said Letters Patent is hereby corrected as shown below:

<u>Column 6,</u>
Line 14, "presons" should be -- present --;
Line 39, "patient," should be -- patient; --;
Line 42, "patients" should be -- patient's --.

Signed and Sealed this

Thirteenth Day of May, 2003

JAMES E. ROGAN
*Director of the United States Patent and Trademark Office*